United States Patent
Wang et al.

(10) Patent No.: US 12,367,582 B1
(45) Date of Patent: Jul. 22, 2025

(54) METHOD AND SYSTEM FOR PROCESSING INTRACRANIAL LARGE VESSEL IMAGE, ELECTRONIC DEVICE, AND MEDIUM

(71) Applicants: Beijing Tiantan Hospital, Capital Medical University, Beijing (CN); BEIHANG UNIVERSITY, Beijing (CN)

(72) Inventors: Yongjun Wang, Beijing (CN); Jing Jing, Beijing (CN); Tao Liu, Beijing (CN); Yanhui Li, Beijing (CN); Lingling Ding, Beijing (CN); Shuo Zhang, Beijing (CN); Pan Liu, Beijing (CN); Ziyang Liu, Beijing (CN); Zixiao Li, Beijing (CN)

(73) Assignees: Beijing Tiantan Hospital, Capital Medical University, Beijing (CN); BEIHANG UNIVERSITY, Beijing (CN)

( * ) Notice: Subject to any disclaimer, the term of this patent is extended or adjusted under 35 U.S.C. 154(b) by 0 days.

(21) Appl. No.: 18/981,835

(22) Filed: Dec. 16, 2024

(51) Int. Cl.
*G06T 7/00* (2017.01)
*A61B 6/03* (2006.01)
(Continued)

(52) U.S. Cl.
CPC ............ *G06T 7/0012* (2013.01); *A61B 6/032* (2013.01); *A61B 6/501* (2013.01); *A61B 6/504* (2013.01); *G06T 7/11* (2017.01); *G06V 10/25* (2022.01); *G06V 10/40* (2022.01); *G06V 10/764* (2022.01); *G06V 10/774* (2022.01); *G06V 10/82* (2022.01);
(Continued)

(58) Field of Classification Search
None
See application file for complete search history.

(56) References Cited

U.S. PATENT DOCUMENTS

2022/0164957 A1* 5/2022 Jia ........................... G16H 50/20
2023/0386029 A1* 11/2023 Seo .................... A61B 5/02007

OTHER PUBLICATIONS

Amukotuwa, Shalini A., et al. "Fast automatic detection of large vessel occlusions on CT angiography." Stroke 50.12 (2019): 3431-3438. (Year: 2019).*

(Continued)

*Primary Examiner* — Samah A Beg
(74) *Attorney, Agent, or Firm* — WC&F IP

(57) ABSTRACT

A method and system for processing an intracranial large vessel image, an electronic device, and a medium are provided. The method includes: acquiring original intracranial large vessel images of a target to be identified and a sample subject; applying a cerebrovascular segmentation model to obtain cerebrovascular mask images; computing regions of interest of the cerebrovascular mask images and bounding boxes; selecting corresponding regions of interest from the original intracranial large vessel images; separately preprocessing the mask image regions of interest and the original image regions of interest to obtain images to be processed; annotating a target region in the image to be processed of the sample subject; training a convolutional neural network model with a training set to obtain a cerebrovascular occlusion classification model; and inputting the image to be processed of the target to be identified to the cerebrovascular occlusion classification model to obtain a target region identification result.

19 Claims, 5 Drawing Sheets

(51) Int. Cl.
    *A61B 6/50*      (2024.01)
    *G06T 7/11*      (2017.01)
    *G06V 10/25*     (2022.01)
    *G06V 10/40*     (2022.01)
    *G06V 10/764*    (2022.01)
    *G06V 10/774*    (2022.01)
    *G06V 10/82*     (2022.01)

(52) U.S. Cl.
    CPC .............. *G06T 2200/04* (2013.01); *G06T 2207/10081* (2013.01); *G06T 2207/20081* (2013.01); *G06T 2207/20084* (2013.01); *G06T 2207/30016* (2013.01); *G06T 2207/30101* (2013.01); *G06V 2201/03* (2022.01)

(56) References Cited

OTHER PUBLICATIONS

Kumar, Shubham, et al. "Mind the Clot: Automated LVO Detection on CTA Using Deep Learning." In Proceedings of the IEEE/CVF International Conference on Computer Vision, pp. 2503-2512. 2023. (Year: 2023).*

Thamm, Florian, et al. "An algorithm for the labeling and interactive visualization of the cerebrovascular system of ischemic strokes." Biomedical Physics & Engineering Express 8.6 (2022): 065016. (Year: 2022).*

CNIPA, Office Action, Application No. 202410223590.8, Apr. 8, 2024.

* cited by examiner

METHOD AND SYSTEM FOR PROCESSING INTRACRANIAL LARGE VESSEL IMAGE, ELECTRONIC DEVICE, AND MEDIUM

CROSS REFERENCE TO RELATED APPLICATION

This patent application claims the benefit and priority of Chinese Patent Application No. 2024102235908, filed with the China National Intellectual Property Administration on Feb. 29, 2024, the disclosure of which is incorporated by reference herein in its entirety as part of the present application.

TECHNICAL FIELD

The present disclosure relates to the technical field of image processing, and in particular, to a method and system for processing an intracranial large vessel image, an electronic device, and a medium.

BACKGROUND

One of common methods to rapidly confirm an intracranial large vessel occlusion or rule out a large vessel occlusion is computed tomography (CT) angiography, which is a three minute quick check and can be easily performed after non-contrastive head CT examination. It can three-dimensionally display the intracranial vascular system and provide important diagnostic basis for occlusive vasculopathy. A radiologist may usually assess a CTA image in as short a time as possible. However, a specific time depends on a plurality of factors, including image quality, the experience and workload of a radiologist, and a workflow of a hospital. Moreover, a position and a severity degree of an occlusion will affect the time of assessment.

Deep learning is one of machine learning methods. For a convolutional neural network, three-dimensional CT angiography features are quite sparse. If a three-dimensional image is input to the convolutional neural network, it is possible that no meaningful target identification result is obtained. Therefore, it is very necessary to select a suitable input.

In terms of preprocessing, maximum intensity projections (MIPs) have been used to facilitate the detection of sudden large vessel occlusions in CT angiography. MIP is a three-dimensional reconstruction technique for medical imaging information, where a voxel having a maximum CT value in a certain thickness (i.e., a CT layer thickness) is protected onto a background plane to display all or part of densely intensified vessels, skeletons, and pulmonary lumps, and obviously intensified soft tissue lesions. In addition, some studies involve firstly using a coarse vascular segmentation algorithm to enhance the expression of sparse vessel features of an image and then obtaining a maximum intensity projection image from a segmentation result.

At present, the identification and classification of intracranial large vessel occlusions generally rely on complicated preprocessing methods, which may lead to information loss. For example, vessel pixels are not identified by a segmentation network or skull voxels are not peeled off clearly when MIP is performed.

SUMMARY

An objective of the present disclosure is to provide a method and system for processing an intracranial large vessel image, an electronic device, and a medium that can improve the accuracy of target region identification.

To achieve the above objective, the present disclosure provides the following technical solutions. A method for processing an intracranial large vessel image includes:
acquiring original intracranial large vessel images of a target to be identified and a sample subject, where the original intracranial large vessel image is a three-dimensional (3D) brain computed tomography (CT) angiography image;
applying a cerebrovascular segmentation model according to the original intracranial large vessel images to obtain cerebrovascular mask images of the target to be identified and the sample subject;
computing regions of interest of the cerebrovascular mask images and bounding boxes of the regions of interest to obtain regions of interest of the mask images of the target to be identified and the sample subject;
selecting corresponding regions of interest from the original intracranial large vessel images according to the bounding boxes of the regions of interest to obtain regions of interest of the original images of the target to be identified and the sample subject;
separately preprocessing the regions of interest of the mask images and the regions of interest of the original images to obtain to-be-processed images of the target to be identified and the sample subject, where the preprocessing includes scaling, normalization, and splicing;
annotating a target region in the to-be-processed image of the sample subject to obtain an annotated image of the sample subject;
training a convolutional neural network model with a training set to obtain a cerebrovascular occlusion classification model, where the training set includes the to-be-processed image of the sample subject and the annotated image of the sample subject; and
inputting the to-be-processed image of the target to be identified to the cerebrovascular occlusion classification model to obtain a target region identification result.

Optionally, the cerebrovascular segmentation model is a nnunet model.

Optionally, the separately preprocessing the regions of interest of the mask images and the regions of interest of the original images to obtain to-be-processed images of the target to be identified and the sample subject specifically includes: scaling the regions of interest of the mask images and the regions of interest of the original images to obtain a region of interest of the mask image and a region of interest of the original image that have a same size;
normalizing the region of interest of the mask image and the region of interest of the original image that have a same size to obtain a normalized region of interest of the mask image and a normalized region of interest of the original image; and
splicing the normalized region of interest of the mask image and the normalized region of interest of the original image to obtain the to-be-processed images of the target to be identified and the sample subject.

Optionally, a max-min normalization method is applied to normalize the region of interest of the mask image and the region of interest of the original image that have a same size.

Optionally, the method for processing an intracranial large vessel image further includes: performing data enhancement on the training set, where the data enhancement includes random scaling, random rotation, and random translation.

Optionally, a structure of the convolutional neural network model includes one feature extractor, two one-dimensional linear layers, and a Sigmoid activation function that are connected in sequence.

The feature extractor includes a first extraction module, a second extraction module, a third extraction module, a fourth extraction module, a fifth extraction module, and a sixth extraction module that are connected in sequence; the first extraction module includes one convolution unit and one residual block based on an attention mechanism that are connected in sequence; each of the second extraction module, the third extraction module, the fourth extraction module, the fifth extraction module, and the sixth extraction module includes one maximum pooling layer, one convolution unit, and one residual block based on the attention mechanism that are connected in sequence; the convolution unit includes a convolutional layer, a group normalization layer, and a rectified linear unit (ReLU) activation function that are connected in sequence; and the residual block based on the attention mechanism includes two convolutional layers and one channel attention mechanism module that are connected in sequence.

Optionally, a training process of the convolutional neural network model specifically includes: performing label smoothing regularization on the annotated image of the sample subject to obtain a smoothed label;

inputting the to-be-processed image of the sample subject to the convolutional neural network model to obtain an output label;

computing a cross-entropy loss of a multiclass label according to the smoothed label and the output label; and training the convolutional neural network model according to the cross-entropy loss of the multiclass label.

A system for processing an intracranial large vessel image is applied to the method for processing an intracranial large vessel image described above, and includes an acquisition module, a segmentation module, a computation module, a selection module, a preprocessing module, an annotation module, a training module, and a classification module.

The acquisition module is configured to acquire original intracranial large vessel images of a target to be identified and a sample subject, where the original intracranial large vessel image is a 3D brain CT angiography image.

The segmentation module is configured to apply a cerebrovascular segmentation model according to the original intracranial large vessel images to obtain cerebrovascular mask images of the target to be identified and the sample subject.

The computation module is configured to compute regions of interest of the cerebrovascular mask images and bounding boxes of the regions of interest to obtain regions of interest of the mask images of the target to be identified and the sample subject.

The selection module is configured to select corresponding regions of interest from the original intracranial large vessel images according to the bounding boxes of the regions of interest to obtain regions of interest of the original images of the target to be identified and the sample subject.

The preprocessing module is configured to separately preprocess the regions of interest of the mask images and the regions of interest of the original images to obtain to-be-processed images of the target to be identified and the sample subject, where the preprocessing includes scaling, normalization, and splicing.

The annotation module is configured to annotate a target region in the to-be-processed image of the sample subject to obtain an annotated image of the sample subject.

The training module is configured to train a convolutional neural network model with a training set to obtain a cerebrovascular occlusion classification model, where the training set includes the to-be-processed image of the sample subject and the annotated image of the sample subject.

The classification module is configured to input the to-be-processed image of the target to be identified to the cerebrovascular occlusion classification model to obtain a target region identification result.

An electronic device includes a memory and a processor, where the memory is configured to store a computer program, and the processor is configured to run the computer program to cause the electronic device to perform the method for processing an intracranial large vessel image described above.

A computer readable storage medium stores a computer program which, when executed by a processor, implements the method for processing an intracranial large vessel image described above.

According to specific embodiments provided in the present disclosure, the present disclosure has the following technical effects: According to the present disclosure, firstly, the cerebrovascular segmentation model is utilized to segment an original three-dimensional CT angiography image and combine the original three-dimensional CT angiography image with the segmented image information. The convolutional neural network model is trained with the training set to obtain the cerebrovascular occlusion classification model, where the training set includes a combined image of the original three-dimensional CT angiography image and the segmented image information for a sample subject and a corresponding annotated image. A combined image of the original three-dimensional CT angiography image and the segmented image information for a target to be identified is input to the cerebrovascular occlusion classification model to obtain a target region identification result. The purpose of improving the accuracy of target region identification is improved.

BRIEF DESCRIPTION OF THE DRAWINGS

To describe the technical solutions in embodiments of the present disclosure or in the prior art more clearly, the accompanying drawings required in the embodiments are briefly described below. Apparently, the accompanying drawings in the following description show merely some embodiments of the present disclosure, and other drawings can be derived from these accompanying drawings by those of ordinary skill in the art without creative efforts.

DETAILED DESCRIPTION OF THE EMBODIMENTS

The technical solutions of the embodiments of the present disclosure are clearly and completely described below with reference to the accompanying drawings. Apparently, the described embodiments are merely a part rather than all of the embodiments of the present disclosure. All other embodiments obtained by a person of ordinary skill in the art on the basis of the embodiments of the present invention without creative efforts shall fall within the protection scope of the present invention.

An objective of the present disclosure is to provide a method and system for processing an intracranial large vessel image, an electronic device, and a medium that can improve the accuracy of target region identification.

The technical overall route of the present disclosure is as follows: firstly, a pre-trained accurate cerebrovascular segmentation model is employed to segment an initial brain CT angiography image to obtain a cerebrovascular mask. A bounding box of a region of interest is then calculated according to the mask, and the brain CT angiography image and the mask are preprocessed using the bounding box to construct a classification network input. Subsequently, based on a multi-task multi-label classification learning method, a suitable loss function is employed to train a classification model. Finally, the pre-trained cerebrovascular segmentation model and the cerebrovascular occlusion classification model are integrated to identify a target region of the initial brain CT angiography image of a target to be identified.

To make the above objectives, features, and advantages of the present disclosure clearer and more comprehensible, the present disclosure will be further described in detail below with reference to the accompanying drawings and the specific embodiments.

Figure 5:
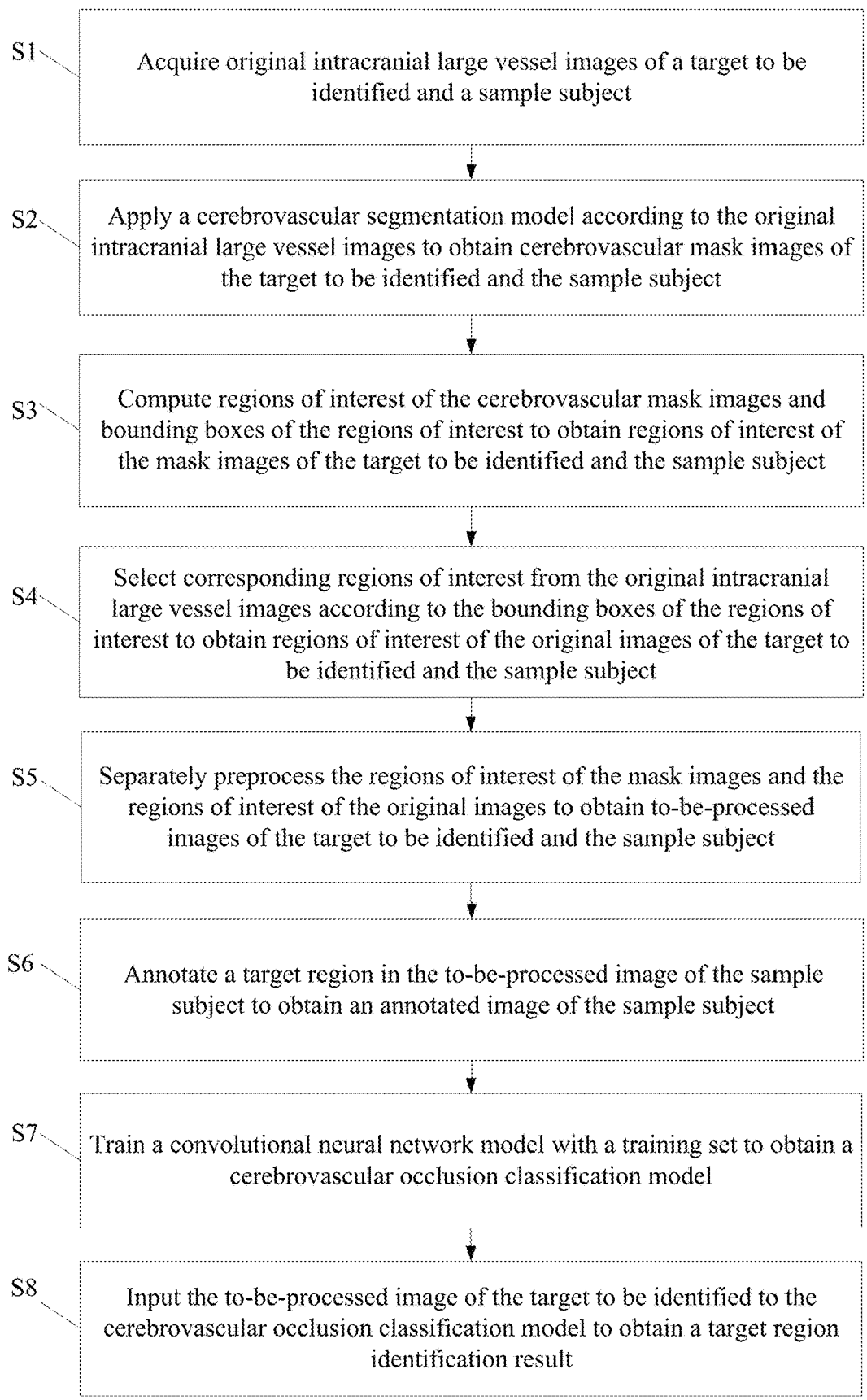
FIG. 5 is a flowchart of a method for processing an intracranial large vessel image according to the present disclosure.

Example 1: As shown in FIG. 5, the present disclosure provides a method for processing an intracranial large vessel image, including steps S1 to S8.

In step S1, original intracranial large vessel images of a target to be identified and a sample subject are acquired, where the original intracranial large vessel image is a 3D brain CT angiography image.

In step S2, a cerebrovascular segmentation model is applied according to the original intracranial large vessel images to obtain cerebrovascular mask images of the target to be identified and the sample subject.

Specifically, the cerebrovascular segmentation model is a nnunet model.

In step S3, regions of interest of the cerebrovascular mask images and bounding boxes of the regions of interest are computed to obtain regions of interest of the mask images of the target to be identified and the sample subject.

In step S4, corresponding regions of interest are selected from the original intracranial large vessel images according to the bounding boxes of the regions of interest to obtain regions of interest of the original images of the target to be identified and the sample subject.

In step S5, the regions of interest of the mask images and the regions of interest of the original images are separately preprocessed to obtain to-be-processed images of the target to be identified and the sample subject, where the preprocessing includes scaling, normalization, and splicing.

Step S5 specifically includes the steps S51 to S53.

In step S51, the regions of interest of the mask images and the regions of interest of the original images are scaled to obtain a region of interest of the mask image and a region of interest of the original image that have a same size.

In step S52, the region of interest of the mask image and the region of interest of the original image that have a same size are normalized to obtain a normalized region of interest of the mask image and a normalized region of interest of the original image.

Specifically, a max-min normalization method is applied to normalize the region of interest of the mask image and the region of interest of the original image that have a same size.

In step S53, the normalized region of interest of the mask image and the normalized region of interest of the original image are spliced to obtain the to-be-processed images of the target to be identified and the sample subject.

In step S6, a target region in the to-be-processed image of the sample subject is annotated to obtain an annotated image of the sample subject.

In step S7, a convolutional neural network model is trained with a training set to obtain a cerebrovascular occlusion classification model, where the training set includes the to-be-processed image of the sample subject and the annotated image of the sample subject.

Before training the convolutional neural network model, the method for processing an intracranial large vessel image further includes the following step: data enhancement is performed on the training set, where the data enhancement includes random scaling, random rotation, and random translation.

In practical application, since human body differences and imaging processes may result in inconsistency of images in an actual situation, three basic data enhancement manners: random scaling, random rotation, and random translation, are employed in the present disclosure. In order to guarantee that only a small image change is caused, ranges of scaling, a rotation angle, and translation are set to from 0.9 to 1.2, −30° to 30°, and −10 to 10, respectively. Note that the same data enhancement processing is performed on an angiography image and a mask in training in order to ensure a one-to-one correspondence therebetween.

In addition, for an application scenario of the present disclosure, due to factors such as a machine, an environment, and a contrast agent injection time, a cerebrovascular region in an image may be dim and faint such that a region of interest might be difficultly concerned by the model. In order to enhance the adaptability of the model to this phenomenon, the cerebrovascular region of the original image is adjusted with respect to a gray value using the mask in the present disclosure, with an adjustment factor being set to from 0.9 to 1.2.

Enhancing the diversity of a dataset is a common data processing manner in deep learning, which can improve the performance of a computer vision model and help the model to be better generalized to different image changes.

Figure 2:
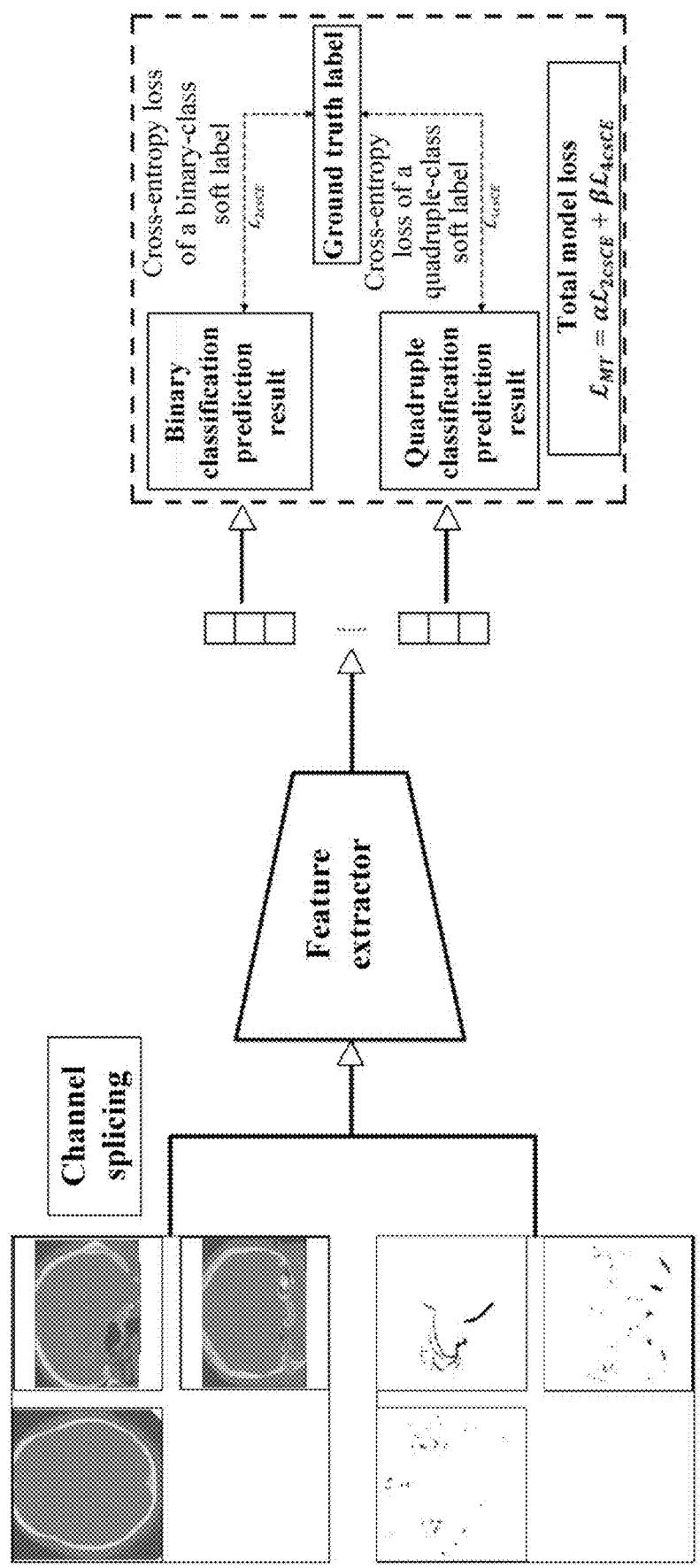
FIG. 2 is a structural schematic diagram of a cerebrovascular occlusion classification model according to the present disclosure.

In a specific embodiment, as shown in FIG. 2, a structure of the convolutional neural network model includes one feature extractor, two one-dimensional linear layers, and a Sigmoid activation function that are connected in sequence. The feature extractor includes a first extraction module, a second extraction module, a third extraction module, a fourth extraction module, a fifth extraction module, and a sixth extraction module that are connected in sequence; the first extraction module includes one convolution unit and one residual block based on an attention mechanism that are connected in sequence; each of the second extraction module, the third extraction module, the fourth extraction module, the fifth extraction module, and the sixth extraction module includes one maximum pooling layer, one convolution unit, and one residual block based on the attention mechanism that are connected in sequence; the convolution unit includes a convolutional layer, a group normalization layer, and a ReLU activation function that are connected in sequence; and the residual block based on the attention mechanism includes two convolutional layers and one channel attention mechanism module that are connected in sequence. Specifically, the residual block based on the attention mechanism includes two same convolutional layers and one channel attention mechanism module that are connected in sequence. In the present disclosure, the first extraction module is stage 1 in FIG. 3; the second extraction module is stage 2 in FIG. 3; the third extraction module is stage 3 in FIG. 3; the fourth extraction module is stage 4 in FIG. 3; the fifth extraction module is stage 5 in FIG. 3; and the sixth extraction module is stage 6 in FIG. 3. The channel attention mechanism module is a squeeze-and-excitation (SE) module in FIG. 3. The residual block based on the attention mechanism is a residual SE module in FIG. 3. One convolution unit is a 3×3×3 3D convolution kernel in FIG. 3.

In practical application, the cerebrovascular occlusion classification model in the present disclosure uses a 3D cerebrovascular CT angiography image of a fixed size and a cerebrovascular mask of a corresponding size as inputs. The 3D cerebrovascular CT angiography image and the cerebrovascular mask are spliced along the direction of a channel and then directly input to the feature extractor, and then extracted features are mapped and vectorized to a feature vector. Finally, two occlusion classification heads are vectors each of which is established using one one-dimensional linear layer plus the Sigmoid activation function and has a final output being a probability value of belong to each class, i.e., vectors having lengths of 2 and 4.

Inputs to the cerebrovascular occlusion classification model of the present disclosure include a cerebrovascular CT angiography image and its cerebrovascular mask obtained after the image is processed by the cerebrovascular segmentation model. A cerebrovascular segmentation network is trained using the existing nnunet framework without any modification. A dataset only needs to be preprocessed and then input to the framework for network training so that a good segmentation effect can be achieved.

Figure 1:
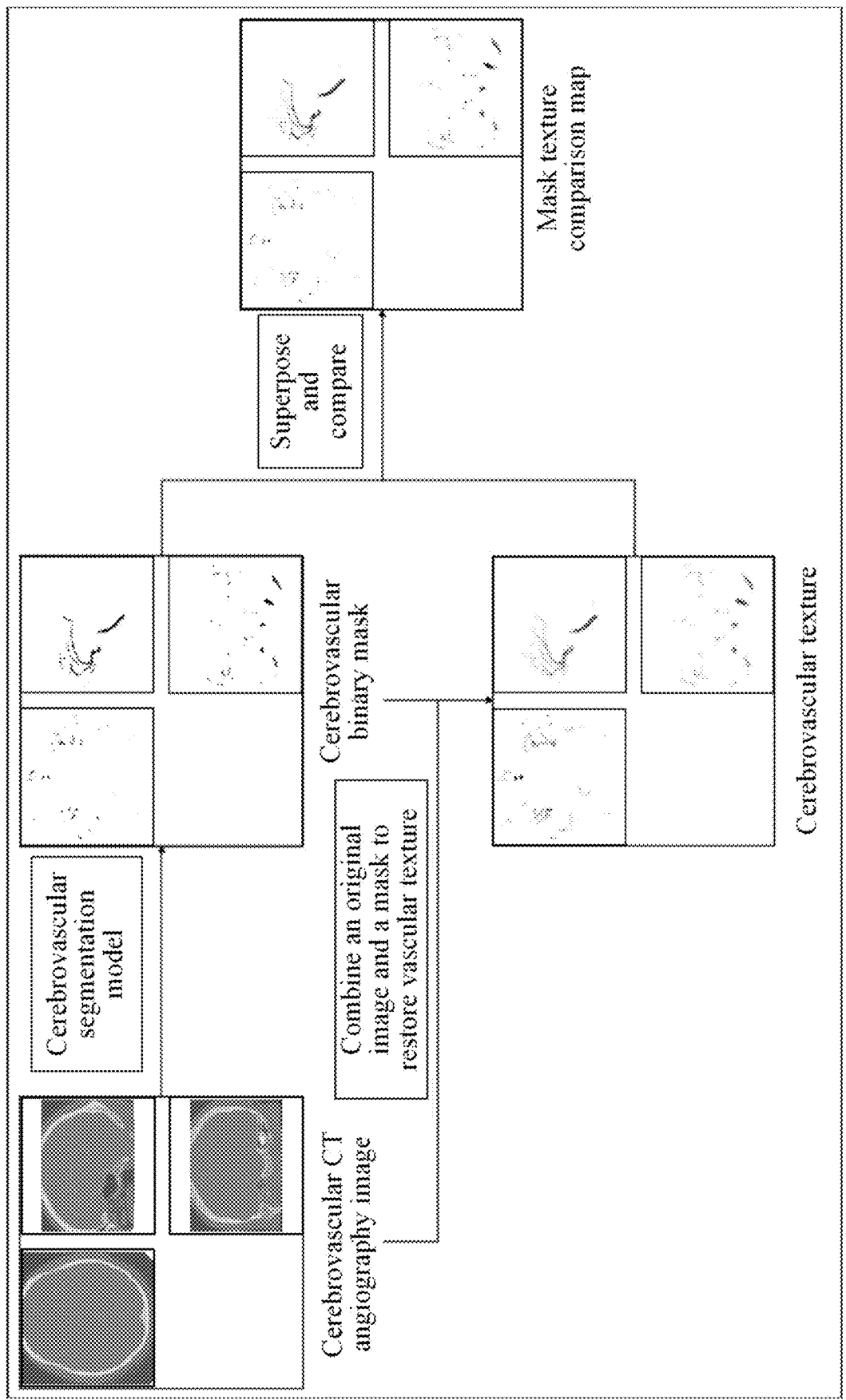
FIG. 1 is a schematic diagram of a process of obtaining a mask result after processing a cerebrovascular CT angiography image according to the present disclosure.

As shown in FIG. 1, the cerebrovascular texture can be restored by combining the original image and the mask. A gray-scale map expression is used in FIG. 1 to clearly show the texture. From a superposed comparison map obtained by superposing and comparing gray-scale texture maps of the original image and the mask image, the region of the vessels in the original image can be correctly represented by the mask part.

A 3D brain image and a cerebrovascular mask are connected in a channel dimension to form a final network input. Further, a shape expression of an image is set to (W, H, D, C)→(image width, image height, image depth, number of channels) and the shape of a 3D brain image is set to (W, H, D, 1). Then, the shape of the cerebrovascular mask obtained after the image is processed by the cerebrovascular segmentation model is also (W, H, D, 1). The 3D brain image and the cerebrovascular mask are superposed in the last dimension to form an image of (W, H, D, 2). The channel image superposition manner is mainly intended to facilitate sending data to the network for training.

Figure 3:
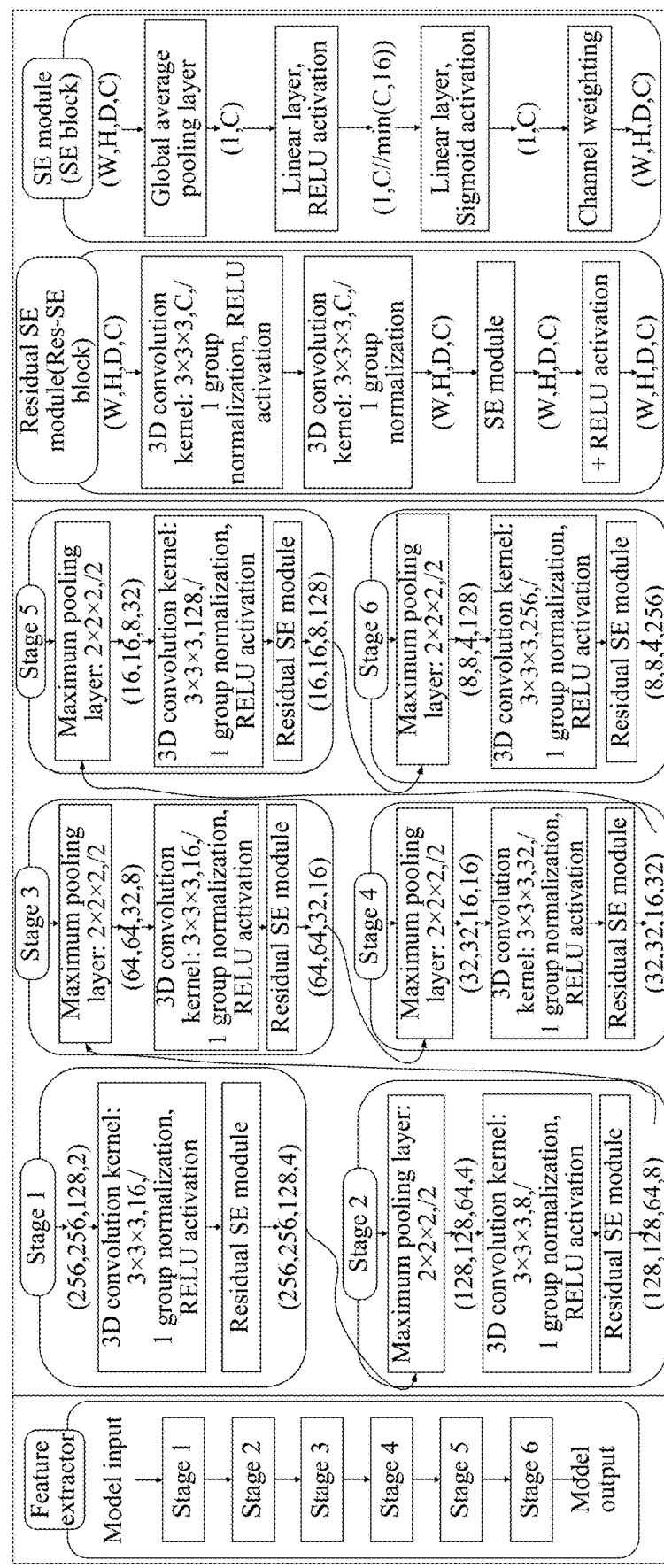
FIG. 3 is a schematic diagram of a convolutional neural network (CNN) architecture designed based on a residual network according to the present disclosure.

The feature extractor may learn and extract information from the input data by convolution, pooling, and other operations. A CNN architecture as shown in FIG. 3 is designed based on a residual network in the present disclosure. The architecture includes six similar stages, each of which includes one convolution unit and one custom residual block (Res-SE block) based on the attention mechanism. The convolution unit includes a 3×3×3 convolutional layer having a stride of 1, one 3D group normalization (GN) layer, and one ReLU activation function. In addition, from the second stage, one 2×2×2 maximum pooling layer having a stride of 2 is added in front of the convolution unit. In a first convolutional block, a number of feature channels is set to 4, and the number is doubled after entering next convolutional block to infer a rich enough vascular information representation. The Res-SE block firstly performs two same convolution operations, and a subsequent SE block can calculate a group of weights. This group of weights is applied to the input so that the feature importance between channels can be enhanced. The SE block firstly performs global average pooling to obtain a global compressed feature vector of a current feature map, and then a weight of each channel is obtained through two fully connected layers. The feature map is weighted using the weight values. Finally, the weighted feature map and the input feature map of the Res-SE block are added up by means of residual connection to form a new feature map for computation of next stage. Such a design can explicitly model an interdependence between network evolution feature channels to improve the quality of representations generated by the network, and can also ameliorate the problems of gradient vanishing and exploding, making training mare stable.

Further, a training process of the convolutional neural network model specifically includes the following steps: label smoothing regularization is performed on the annotated image of the sample subject to obtain a smoothed label.

The to-be-processed image of the sample subject is input to the convolutional neural network model to obtain an output label.

A cross-entropy loss of a multiclass label is computed according to the smoothed label and the output label.

The convolutional neural network model is trained according to the cross-entropy loss of the multiclass label.

In practical application, a loss function used in the present disclosure has been improved based on a multiclass cross-entropy loss. Before computing the loss function, the label smoothing regularization is performed on a ground truth label. It is typically applied to the classification problem, especially the problem having a hard label (one-hot code). The core idea of label smoothing is to, rather than set target labels to strict 0 or 1, adjust them to a probability distribution between 0 and 1. The purpose of doing so is to reduce overfitting of the model to training data such that the model is more robust. In the present disclosure, the following formula is used for label smoothing to obtain a soft label:

$$\hat{y}_{true} = (1-\varepsilon)y_{true} + \frac{\varepsilon}{V},$$

where $y_{true}$ represents an original hard label (i.e., a ground truth label), which is a target label marked by a professional radiologist on a sample and set to strict 0 and 1 (1 represents an occlusion occurring in a corresponding vessel segment, and 0 represents no occlusion); $\varepsilon$ is a smooth factor (a value of which is 0.1 in the present disclosure); and V represents a number of classes of a current classification task. Further, if the radiology department diagnoses that a sample has L-ICA and R-ICA occlusions, $y_{true}$ in a binary classification task is [0, 1] and $y_{true}$ in a quadruple classification task is [1, 1, 0, 0]. After the label smoothing, $\hat{y}_{true}$ is [0.05, 0.95] and [0.925, 0.925, 0.025, 0.025] in the two classification tasks, respectively.

A cross-entropy loss of a multiclass soft label of the smoothed ground truth label $\hat{y}_{true}$ and a network output label $y_{pred}$ is then computed by the following formula:

$$\mathcal{L}_{mcsCE} = \frac{LSE[n_{mask} \odot y_{pred} \odot \log(1 - \hat{y}_{true})] + LSE[p_{mask} \odot (-y_{pred}) \odot \log(\hat{y}_{true})]}{2};$$

where $n_{mask}$ and $p_{mask}$ represent two Boolean masks, which represent a value less than or equal to 1-$\hat{\varepsilon}$ and a value greater than or equal to $\hat{\varepsilon}$ in $\hat{y}_{true}$, respectively; $\hat{\varepsilon}$ is decimals very close to zero, which may be set to 1e-7 or 1e-6 and used to avoid that numerical values divided in deep learning are unstable and to filter out invalid values in labels; $\odot$ is a Hadamard product (an element-by-element product, a binary operation); LSE( ) represents averaging after performing element-by-element logsumexp operation on elements in a tensor; and $\mathcal{L}_{mcsCE}$ represents the cross-entropy loss.

The present disclosure uses a multi-task learning structure synchronously trained with binary classification and quadruple classification, and the final loss is defined as the following formula. $\mathcal{L}_{2csCE}$ and $\mathcal{L}_{4csCE}$ represent a cross-entropy loss of a binary-class soft label and a cross-entropy loss of a quadruple-class soft label, respectively; and α and β represent adjustment factors of loss weights of different classification tasks (values of which are 0.25 and 0.75 in the present disclosure), respectively.

$$\mathcal{L}_{MT} = \alpha \mathcal{L}_{2csCE} + \beta \mathcal{L}_{4scCE}.$$

In step S8, the to-be-processed image of the target to be identified is input to the cerebrovascular occlusion classification model to obtain a target region identification result.

Figure 4:
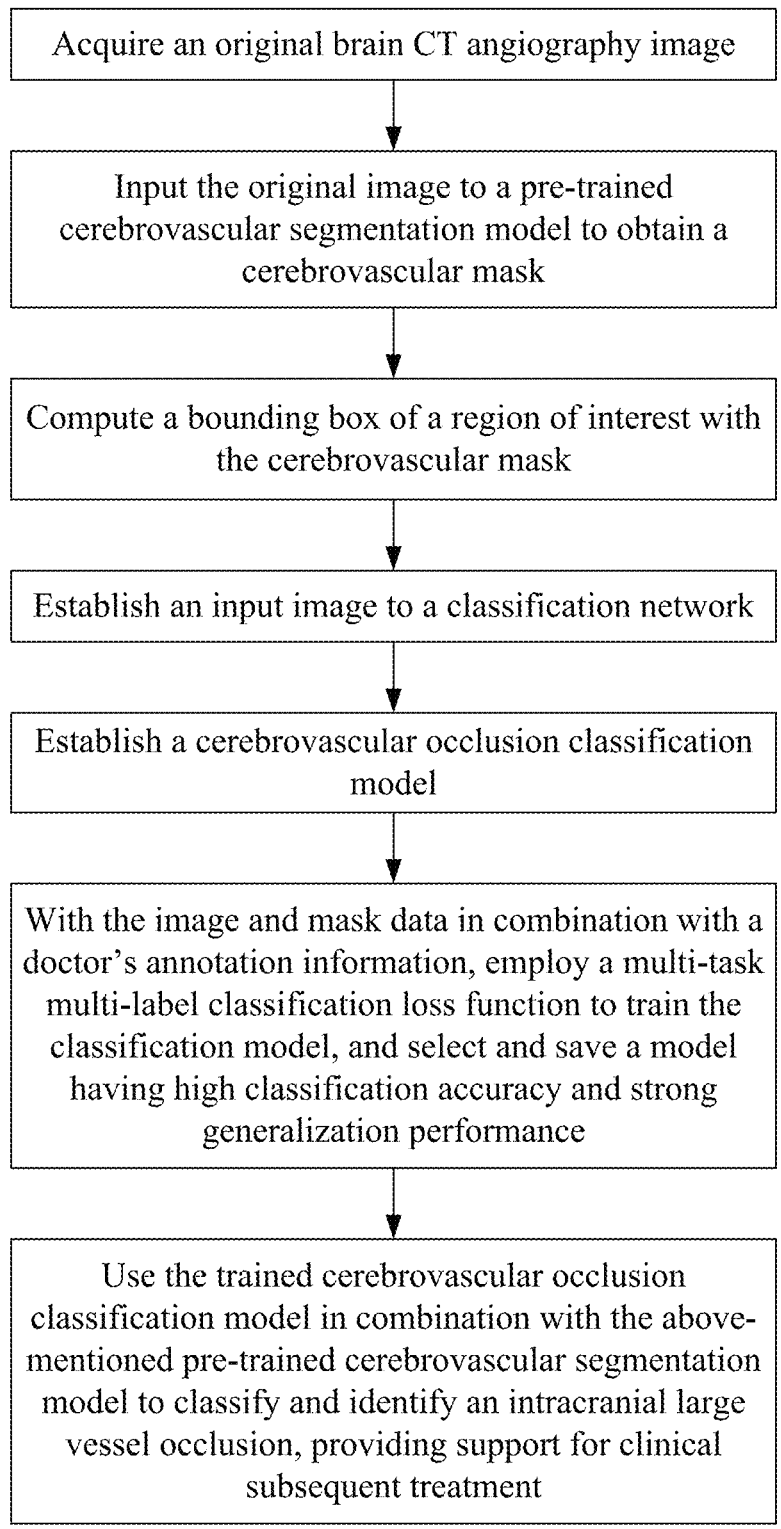
FIG. 4 is a diagram of an actual application workflow of a method for processing an intracranial large vessel image according to the present disclosure.

As shown in FIG. 4, the main workflow of the method for processing an intracranial large vessel image provided in the present disclosure is as follows: (1) An original image is acquired. Specifically, the original image is a 3D brain CT angiography image.

(2) The original image is input to a pre-trained cerebrovascular segmentation model to obtain a cerebrovascular mask.

Specifically, an accurate cerebrovascular segmentation network is used to segment an image containing context information to obtain a cerebrovascular segmentation mask of the original 3D brain CT angiography image. The existing nnunet framework is used for training without any modification. A dataset only needs to be preprocessed and then input to the framework for network training so that a good segmentation effect can be achieved.

(3) A bounding box of a region of interest is computed with the cerebrovascular mask.

Specifically, the bounding box is used for identifying and framing a position of the region of interest in visual data. With the mask information, a minimum 3D bounding box capable of framing all brain vessels therein can be found. In order to reduce boundary errors of the segmentation model while not ignoring the vessel edge tissue information of the original image, enlargement is performed by 10 voxels along each of 6 directions of x, y, and z axes.

(4) An input image to a classification network is established.

Specifically, the original image and the cerebrovascular mask are preprocessed. On the one hand, the accuracy of predicting a brain age by the deep learning method can be improved; and on the other hand, the speed of processing and analysis is increased. High efficiency and ease of use are achieved. The preprocessing includes (4.1) to (4.3).

(4.1) The original image and the cerebrovascular mask are box-selected using the bounding box, and the shapes of them are selected to 256×256×128.

(4.2) Window width normalization: in order to better display vascular details, a window width is set to [−1024, 2048]. That is, both of a part having a CT value less than −1024 and a part above 2048 are set as upper and lower limits of the window width. Max-min normalization (the formula of which is shown below) is then used to scale all pixels of the image to from 0 to 1. In the following formula, $x_i$ represents a gray value of a certain pixel in a 3D image x; and min(x) and max(x) represent a pixel minimum and maximum of the image x, respectively.

$$norm(x_i) = \frac{x_i - \min(x)}{\max(x) - \min(x)}.$$

(4.3) The preprocessed brain image and cerebrovascular mask are connected in the channel dimension to form a network input in dimensions [256, 256, 128, 2].

(5) A cerebrovascular occlusion classification model is established.

(6) Using the image and mask data in combination with a doctor's annotation information, a multi-task multi-label classification loss function is employed to train the classification model, and a model having high classification accuracy and strong generalization performance is selected and saved.

(7) The trained cerebrovascular occlusion classification model is used in combination with the above-mentioned pre-trained cerebrovascular segmentation model to classify and identify an intracranial large vessel occlusion, providing support for clinical subsequent treatment.

The present disclosure has the following advantages: 1. The present disclosure uses the deep learning method and can identify and classify an intracranial large vessel occlusion only through CT angiography without complicated preprocessing steps.

2. The present disclosure proposes a multi-mask learning classification network architecture that can perform binary classification and quadruple classification tasks simultaneously and can improve the accuracy of classification results.

3. The present disclosure uses the deep learning method to identify and classify an intracranial large vessel occlusion through CT angiography and thus can provide assistance for a doctor's preliminary screening of interpreting an image and diagnosing an occlusion. Specifically, using the deep learning techniques, 4 kinds of specific vessels in which large vessel occlusions occur, namely left internal carotid artery (L-ICA), right internal carotid artery (R-ICA), and left branch (L-M1) and right branch (R-M1) of middle cerebral artery M1 segment, are taken as target regions for identification.

4. The method proposed in the present disclosure does not need complicated image preprocessing steps. The whole flow only requires original CT angiography data. Information is not prone to loss. The accuracy of the identification results is improved.

Example 2: In order to perform the corresponding method of Example 1 to achieve the corresponding functions and technical effects, a system for processing an intracranial large vessel image is provided below, which includes an acquisition module, a segmentation module, a computation module, a selection module, a preprocessing module, an annotation module, a training module, and a classification module.

The acquisition module is configured to acquire original intracranial large vessel images of a target to be identified and a sample subject, where the original intracranial large vessel image is a 3D brain CT angiography image.

The segmentation module is configured to apply a cerebrovascular segmentation model according to the original intracranial large vessel images to obtain cerebrovascular mask images of the target to be identified and the sample subject.

The computation module is configured to compute regions of interest of the cerebrovascular mask images and bounding boxes of the regions of interest to obtain regions of interest of the mask images of the target to be identified and the sample subject.

The selection module is configured to select corresponding regions of interest from the original intracranial large vessel images according to the bounding boxes of the regions of interest to obtain regions of interest of the original images of the target to be identified and the sample subject.

The preprocessing module is configured to separately preprocess the regions of interest of the mask images and the regions of interest of the original images to obtain to-be-processed images of the target to be identified and the sample subject, where the preprocessing includes scaling, normalization, and splicing.

The annotation module is configured to annotate a target region in the to-be-processed image of the sample subject to obtain an annotated image of the sample subject.

The training module is configured to train a convolutional neural network model with a training set to obtain a cerebrovascular occlusion classification model, where the training set includes the to-be-processed image of the sample subject and the annotated image of the sample subject.

The classification module is configured to input the to-be-processed image of the target to be identified to the cerebrovascular occlusion classification model to obtain a target region identification result.

Example 3: This example of the present disclosure provides an electronic device, including a memory and a processor, where the memory is configured to store a computer program; and the processor is configured to run the computer program to cause the electronic device to perform the method for processing an intracranial large vessel image of Example 1.

Optionally, the electronic device may be a server.

In addition, an embodiment of the present disclosure further provides a computer readable storage medium, storing a computer program which, when executed by a processor, implements the method for processing an intracranial large vessel image of Example 1.

The embodiments are described herein in a progressive manner. Each embodiment focuses on the difference from another embodiment, and the same and similar parts between the embodiments may refer to each other. Since the system disclosed in the embodiments corresponds to the method disclosed in the embodiments, the description is relatively simple, and reference can be made to the method description.

Specific examples are used herein to explain the principles and implementations of the present disclosure. The foregoing description of the embodiments is merely intended to help understand the method of the present disclosure and its core ideas; besides, various modifications may be made by a person of ordinary skill in the art to specific embodiments and the scope of application in accordance with the ideas of the present disclosure. In conclusion, the content of this specification shall not be construed as limitations to the present disclosure.

What is claimed is:

1. A method for processing an intracranial large vessel image, comprising:

acquiring original intracranial large vessel images of a target to be identified and a sample subject, wherein the original intracranial large vessel image is a three-dimensional (3D) brain computed tomography (CT) angiography image;

applying a cerebrovascular segmentation model according to the original intracranial large vessel images to obtain cerebrovascular mask images of the target to be identified and the sample subject;

computing regions of interest of the cerebrovascular mask images and bounding boxes of the regions of interest to obtain regions of interest of the mask images of the target to be identified and the sample subject;

selecting corresponding regions of interest from the original intracranial large vessel images according to the bounding boxes of the regions of interest to obtain regions of interest of the original images of the target to be identified and the sample subject;

separately preprocessing the regions of interest of the mask images and the regions of interest of the original images to obtain to-be-processed images of the target to be identified and the sample subject, wherein the preprocessing comprises scaling, normalization, and splicing;

annotating a target region in the to-be-processed image of the sample subject to obtain an annotated image of the sample subject;

training a convolutional neural network model with a training set to obtain a cerebrovascular occlusion classification model, wherein the training set comprises the to-be-processed image of the sample subject and the annotated image of the sample subject; and inputting the to-be-processed image of the target to be identified to the cerebrovascular occlusion classification model to obtain a target region identification result;

wherein a training process of the convolutional neural network model specifically comprises:

performing label smoothing regularization on the annotated image of the sample subject to obtain a smoothed label, wherein a computational formula is as follows:

$$\hat{y}_{true} = (1 - \varepsilon)y_{true} + \frac{\varepsilon}{V},$$

wherein $y_{true}$ represents an original hard label, namely a ground truth label, which is a target label marked by a professional radiologist on a sample and set to strict 0 and 1; $\varepsilon$ is a smooth factor; $V$ represents a number of classes of a current classification task; and $\hat{y}_{true}$ represents the smoothed label;

inputting the to-be-processed image of the sample subject to the convolutional neural network model to obtain an output label, $y_{pred}$;

computing a cross-entropy loss of a multiclass label according to the smoothed label and the label, wherein a computational formula is as follows: output $$\mathcal{L}_{mcsCE} = \frac{LSE[n_{mask} \odot y_{pred} \odot \log(1 - \hat{y}_{true})] + LSE[p_{mask} \odot (-y_{pred}) \odot \log(\hat{y}_{true})]}{2},$$

wherein $n_{mask}$ and $p_{mask}$ represent two Boolean masks, which represent a value less than or equal to $1-\hat{\epsilon}$ and a value greater than or equal to $\hat{\epsilon}$ in $\hat{y}_{true}$, respectively; $\hat{\epsilon}$ is decimals very close to zero, which is set to 1e-7 or 1e-6; $\odot$ is a Hadamard product; LSE( ) represents averaging after performing element-by-element logsumexp operation on elements in a tensor; and $\mathcal{L}_{mcsCE}$ represents the cross-entropy loss; and training the convolutional neural network model according to the cross-entropy loss of the multiclass label.

2. The method for processing an intracranial large vessel image according to claim 1, wherein the cerebrovascular segmentation model is a nnunet model.

3. The method for processing an intracranial large vessel image according to claim 1, wherein the separately preprocessing the regions of interest of the mask images and the regions of interest of the original images to obtain to-be-processed images of the target to be identified and the sample subject specifically comprises:

scaling the regions of interest of the mask images and the regions of interest of the original images to obtain a region of interest of the mask image and a region of interest of the original image that have a same size;

normalizing the region of interest of the mask image and the region of interest of the original image that have a same size to obtain a normalized region of interest of the mask image and a normalized region of interest of the original image; and splicing the normalized region of interest of the mask image and the normalized region of interest of the original image to obtain the to-be-processed images of the target to be identified and the sample subject.

4. The method for processing an intracranial large vessel image according to claim 3, wherein a max-min normalization method is applied to normalize the region of interest of the mask image and the region of interest of the original image that have a same size.

5. The method for processing an intracranial large vessel image according to claim 1, further comprising:

performing data enhancement on the training set, wherein the data enhancement comprises random scaling, random rotation, and random translation.

6. The method for processing an intracranial large vessel image according to claim 1, wherein a structure of the convolutional neural network model comprises one feature extractor, two one-dimensional linear layers, and a Sigmoid activation function that are connected in sequence; and the feature extractor comprises a first extraction module, a second extraction module, a third extraction module, a fourth extraction module, a fifth extraction module, and a sixth extraction module that are connected in sequence; the first extraction module comprises one convolution unit and one residual block based on an attention mechanism that are connected in sequence; each of the second extraction module, the third extraction module, the fourth extraction module, the fifth extraction module, and the sixth extraction module comprises one maximum pooling layer, one convolution unit, and one residual block based on the attention mechanism that are connected in sequence; the convolution unit comprises a convolutional layer, a group normalization layer, and a rectified linear unit (ReLU) activation function that are connected in sequence; and the residual block based on the attention mechanism comprises two convolutional layers and one channel attention mechanism module that are connected in sequence.

7. A system for processing an intracranial large vessel image, comprising:

an acquisition module configured to acquire original intracranial large vessel images of a target to be identified and a sample subject, wherein the original intracranial large vessel image is a 3D brain CT angiography image;

a segmentation module configured to apply a cerebrovascular segmentation model according to the original intracranial large vessel images to obtain cerebrovascular mask images of the target to be identified and the sample subject;

a computation module configured to compute regions of interest of the cerebrovascular mask images and bounding boxes of the regions of interest to obtain regions of interest of the mask images of the target to be identified and the sample subject;

a selection module configured to select corresponding regions of interest from the original intracranial large vessel images according to the bounding boxes of the regions of interest to obtain regions of interest of the original images of the target to be identified and the sample subject;

a preprocessing module configured to separately preprocess the regions of interest of the mask images and the regions of interest of the original images to obtain to-be-processed images of the target to be identified and the sample subject, wherein the preprocessing comprises scaling, normalization, and splicing;

an annotation module configured to annotate a target region in the to-be-processed image of the sample subject to obtain an annotated image of the sample subject;

a training module configured to train a convolutional neural network model with a training set to obtain a cerebrovascular occlusion classification model, wherein the training set comprises the to-be-processed image of the sample subject and the annotated image of the sample subject; and a classification module configured to input the to-be-processed image of the target to be identified to the cerebrovascular occlusion classification model to obtain a target region identification result;

wherein a training process of the convolutional neural network model specifically comprises:

performing label smoothing regularization on the annotated image of the sample subject to obtain a smoothed label, wherein a computational formula is as follows:

$$\hat{y}_{true} = (1 - \varepsilon) y_{true} + \frac{\varepsilon}{V},$$

wherein $y_{true}$ represents an original hard label, namely a ground truth label, which is a target label marked by a professional radiologist on a sample and set to strict 0 and 1; ε is a smooth factor; V represents a number of classes of a current classification task; and $\hat{y}_{true}$ represents the smoothed label;

inputting the to-be-processed image of the sample subject to the convolutional neural network model to obtain an output label, $y_{pred}$;

computing a cross-entropy loss of a multiclass label according to the smoothed label and the output label, wherein a computational formula is as follows:

$$\mathcal{L}_{mcsCE} = \frac{LSE[n_{mask} \odot y_{pred} \odot \log(1 - \hat{y}_{true})] + LSE[p_{mask} \odot (-y_{pred}) \odot \log(\hat{y}_{true})]}{2},$$

wherein $n_{mask}$ and $p_{mask}$ represent two Boolean masks, which represent a value less than or equal to 1−ε and a value greater than or equal to $\hat{\varepsilon}$ in $\hat{y}_{true}$, respectively; $\hat{\varepsilon}$ is decimals very close to zero, which is set to 1e-7 or 1e-6; ⊙ is a Hadamard product; LSE( ) represents averaging after performing element-by-element logsumexp operation on elements in a tensor; and $\mathcal{L}_{mcsCE}$ represents the cross-entropy loss; and training the convolutional neural network model according to the cross-entropy loss of the multiclass label.

8. An electronic device, comprising a memory and a processor, wherein the memory is configured to store a computer program, and the processor is configured to run the computer program to cause the electronic device to perform the method for processing an intracranial large vessel image according to claim 1.

9. A non-transitory computer readable storage medium, storing a computer program which, when executed by a processor, implements the method for processing an intracranial large vessel image according to claim 1.

10. An electronic device, comprising a memory and a processor, wherein the memory is configured to store a computer program, and the processor is configured to run the computer program to cause the electronic device to perform the method for processing an intracranial large vessel image according to claim 2.

11. An electronic device, comprising a memory and a processor, wherein the memory is configured to store a computer program, and the processor is configured to run the computer program to cause the electronic device to perform the method for processing an intracranial large vessel image according to claim 3.

12. An electronic device, comprising a memory and a processor, wherein the memory is configured to store a computer program, and the processor is configured to run the computer program to cause the electronic device to perform the method for processing an intracranial large vessel image according to claim 4.

13. An electronic device, comprising a memory and a processor, wherein the memory is configured to store a computer program, and the processor is configured to run the computer program to cause the electronic device to perform the method for processing an intracranial large vessel image according to claim 5.

14. An electronic device, comprising a memory and a processor, wherein the memory is configured to store a computer program, and the processor is configured to run the computer program to cause the electronic device to perform the method for processing an intracranial large vessel image according to claim 6.

15. A non-transitory computer readable storage medium, storing a computer program which, when executed by a processor, implements the method for processing an intracranial large vessel image according to claim 2.

16. A non-transitory computer readable storage medium, storing a computer program which, when executed by a processor, implements the method for processing an intracranial large vessel image according to claim 3.

17. A non-transitory computer readable storage medium, storing a computer program which, when executed by a processor, implements the method for processing an intracranial large vessel image according to claim 4.

18. A non-transitory computer readable storage medium, storing a computer program which, when executed by a processor, implements the method for processing an intracranial large vessel image according to claim 5.

19. A non-transitory computer readable storage medium, storing a computer program which, when executed by a processor, implements the method for processing an intracranial large vessel image according to claim 6.

* * * * *